United States Patent [19]

Sakuma et al.

[11] Patent Number: 5,166,169
[45] Date of Patent: Nov. 24, 1992

[54] TREATING AGENT FOR PERIPHERAL CIRCULATORY DISTURBANCES

[75] Inventors: Kyoko Sakuma; Shinichiro Ashida, both of Tokyo, Japan

[73] Assignee: Daiichi Pharmaceutical Co., Ltd., Tokyo, Japan

[21] Appl. No.: 696,254

[22] Filed: Apr. 30, 1991

Related U.S. Application Data

[63] Continuation of Ser. No. 367,578, Jun. 19, 1989, abandoned.

[30] Foreign Application Priority Data

Jun. 17, 1988 [JP] Japan .................................. 63-149445

[51] Int. Cl.$^5$ ................. A61K 31/415; A61K 31/425; A61K 31/435
[52] U.S. Cl. ................................ 514/399; 514/277; 514/365; 514/372; 514/403
[58] Field of Search ............... 514/277, 365, 372, 399, 514/403

[56] References Cited

U.S. PATENT DOCUMENTS 4,665,188  5/1987  Kanao .................................. 548/341
4,777,257  10/1988  Kanao .................................. 548/341

FOREIGN PATENT DOCUMENTS 61-191612  8/1986  Japan .

Primary Examiner—Allen J. Robinson
Attorney, Agent, or Firm—Sughrue, Mion, Zinn, Macpeak & Seas

[57] ABSTRACT

A preventing and treating agent for peripheral circulatory disturbances containing a compound represented by formula (I):

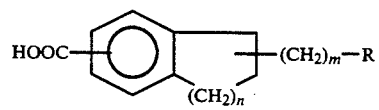

(I)

wherein R represents an imidazolyl group, a thiazolyl group, or a pyridyl group; n represents 1 or 2; and m represents an integer of from 1 to 4, or a salt thereof as an active ingredient.

4 Claims, No Drawings

TREATING AGENT FOR PERIPHERAL CIRCULATORY DISTURBANCES

This ia continuation of application Ser. No. 07/367,578 filed Jun. 19, 1989 now abandoned.

FIELD OF THE INVENTION

The invention relates to a treating and preventing agent for peripheral circulatory disturbances containing a compound represented by formula (I):

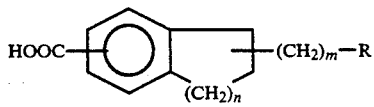

wherein R represents an imidazolyl group, a thiazolyl group, or a pyridyl group; n represents 1 or 2; and m represents an integer of from 1 to 4, or a salt thereof as an active ingredient.

BACKGROUND OF THE INVENTION

The compounds represented by formula (I) are known as treating agents for ischemic heart diseases, as disclosed in U.S. Pat. Nos. 4,665,188 and 4,777,257, but unknown for their activity in prevention and treatment of peripheral circulatory disturbances.

Conventionally available agents for peripheral circulatory disturbances are not sufficiently satisfactory in their effects.

SUMMARY OF THE INVENTION

As a result of intensive and extensive investigations, the inventors have found that the compounds of formula (I) exhibit excellent effects on peripheral circulatory disturbances.

This invention relates to an agent for preventing and treating peripheral circulatory disturbances comprising the compound represented by formula (I) or a salt thereof as an active ingredient.

DETAILED DESCRIPTION OF THE INVENTION

The salts of the compounds of formula (I) which can be used in the present invention include acid addition salts formed with inorganic acids (e.g., hydrochloric acid, sulfuric acid, and nitric acid) or organic acids (e.g., fumaric acid, tartaric acid, maleic acid, succinic acid, and oxalic acid); and alkali metal salts or alkaline earth metal salts formed from the carboxyl group and alkali metals (e.g., sodium and potassium) or alkaline earth metals (e.g., calcium and magnesium).

Peripheral circulatory disturbances on which the compounds of formula (I) and salts thereof are effective include peripheral arterial occlusive diseases, e.g., arteriosclerosis obliterans, Burger disease, and Raynaud disease, etc.

The compounds of formula (I) and salts thereof were tested for acute toxicity $LD_{50}$ in rats (p.o.) and, as a result, proved highly safe.

The compounds of formula (I) and their salts can be formulated in various pharmaceutical preparations, such as tablets, powders, capsules, injectable solutions, and the like, by known pharmaceutical techniques. The compounds of formula (I) or salts thereof are usually administered orally, subcutaneously, intramuscularly, or intravenously.

The dose level of the compounds of formula (I) or salts thereof Vsually ranges from about 100 to about 1,000 mg/day/adult (body weight: about 60 kg) in oral administration.

As demonstrated in Test Example hereinafter given, the compounds of formula (I) and salts thereof exhibited excellent effectiveness in suppressing lesions in a peripheral arterial occlusive disease model, a typical disease model of peripheral circulatory disturbances. The compounds of formula (I) and the salts thereof are therefore excellent as preventing and treating agents for peripheral cicutatory disturbances.

The present invention is now illustrated in greater detail by way of the following Test Examples, but it should be understood that the present invention is not deemed to be limited thereto.

TEST EXAMPLE 1

Effect on Progression of Laurate-Induced Peripheral Arterial Occlusive Diseases in Rats Male Wister-Imamichi rats weighing from 370 to 422 g (purchased from Dobutsu Hanshoku Kenkyukai) were used as test animals.

Rats were anesthetized with pentobarbital (50 mg/kg, i.p.), and the right femoral artery was exposed by surgical incision. 0.1 ml of a sodium laurate solution (1 mg of lauric acid/ml-saline, pH=8.0) was injected to the right femoral artery, haemostasis was secured by application of a surgical binding "Alonalpha" (a trade name, produced by Toa Gosei Kagaku Co.) to the punctured site of the artery, and the incision was closed with the surgical binding. The animals were then fed ad lib.

The animals were observed for progression of the lesions. The degree of the lesions was graded to 0 - IV, 4 days after the operation for gangrene and 6 days after the operation for mummification or falling off as follows normal apperance, 0; the affected region was limited to the nail parts, I; to the fingers, II; to the whole paw, III; and extended to the lower leg, IV.

As a test compound, 6-(1-imidazolylmethyl)-5,6,7,8-tetrahydronaphthalene-2-carboxylic acid hydrochloride ½ hydrate (hereinafter referred to as Compound A) was dissolved in physiological saline and administered to the left femoral vein at a dose of 3 mg/5 ml/kg 5 minutes before the laurate injection to the femoral artery. The effect of the Compound A on suppression of the lesions were examined. The animals in control group were injected with 5 ml/kg of saline alone in place of the Compound A. The results obtained are shown in Table 1 below.

TABLE 1

| | Number of Animals Suffering From: | | | | | | | | | |
| | Gangrene After 4 Days | | | | | Mummification or Falling Off After 6 Days | | | | |
| | 0 | I | II | III | IV | 0 | I | II | III | IV |
| Control Group | | 2 | 1 | | 4 | | 1 | 2 | | 4 |
| Treated Group | 2 | 3 | 2 | | | 2 | 1 | 3 | 1 | |

As is apparent from Table 1, gangrene was seen in the affected paw and the lower leg of the control group 4 days after the injection of the sodium laurate solution, and the gangrened part mummified or fell off 6 days after the laurate injection. To the contrary, intravenous injection of 3 mg/kg of the Compound A reduced the grade of lesions.

Accordingly, it was confirmed that the Compound A is useful for the prevention and treatment of peripheral arterial occlusive diseases, i.e., peripheral circulatory disturbances.

TEST EXAMPLE 2

Acute toxicity of the Compound A in rats (p.o.) is shown in Table 2.

TABLE 2

| Acute Toxicity (rat, p.o.) $LD_{50}$ (mg/kg) | |
| --- | --- |
| Male | Female |
| 2438 | 1994 |

While the invention has been described in detail and with reference to specific embodiments thereof, it will be apparent to one skilled in the art that various changes and modifications can be made therein without departing from the spirit and scope thereof.

What is claimed is:

1. A method for preventing or treating peripheral arterial occlusive diseases comprising administering to a human host in need of treatment a composition comprising a therapeutically effective amount of 6-(1-imidazolylmethyl)-5,6,7,8-tetrahydronaphthalene-2-carboxylic acid, or pharmaceutically acceptable salts thereof and a pharmaceutically acceptable carrier.

2. The method of claim 1 wherein said disease is arteriosclerosis obliterans.

3. The method of claim 1 wherein said disease is Burger disease.

4. The method of claim 1 wherein said disease is Raynaud disease.

* * * * *